United States Patent
Li et al.

(10) Patent No.: US 10,206,634 B2
(45) Date of Patent: Feb. 19, 2019

(54) DOSE BASED X-RAY SCANNING

(71) Applicant: SHENYANG NEUSOFT MEDICAL SYSTEMS CO., LTD., Shenyang, Liaoning (CN)

(72) Inventors: Shuangxue Li, Shenyang (CN); Ling Pang, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 523 days.

(21) Appl. No.: 14/843,749

(22) Filed: Sep. 2, 2015

(65) Prior Publication Data
US 2016/0058405 A1 Mar. 3, 2016

(30) Foreign Application Priority Data
Sep. 2, 2014 (CN) .......................... 2014 1 0446011

(51) Int. Cl.
*A61B 6/03* (2006.01)
*A61B 6/00* (2006.01)

(52) U.S. Cl.
CPC ............ *A61B 6/032* (2013.01); *A61B 6/5258* (2013.01); *A61B 6/5294* (2013.01); *A61B 6/542* (2013.01); *A61B 6/545* (2013.01)

(58) Field of Classification Search
None
See application file for complete search history.

(56) References Cited

U.S. PATENT DOCUMENTS

| | | | | |
|---|---|---|---|---|
| 7,103,134 B2 * | 9/2006 | Suzuki | ................... | A61B 6/032 378/4 |
| 7,657,074 B2 * | 2/2010 | Haras | ..................... | A61B 6/032 378/21 |
| 8,218,719 B2 * | 7/2012 | Allmendinger | .... | A61B 5/02405 378/210 |
| 9,615,804 B2 * | 4/2017 | Scheuering | .......... | A61B 6/5205 |
| 9,636,077 B2 * | 5/2017 | Braun | ..................... | A61B 6/545 |
| 9,992,854 B2 * | 6/2018 | Allmendinger | ........ | A61B 6/032 |
| 2003/0123603 A1 * | 7/2003 | Suzuki | ................... | A61B 6/032 378/4 |
| 2004/0101105 A1 | 5/2004 | Segawa et al. | | |
| 2006/0153436 A1 * | 7/2006 | Haras | ..................... | A61B 6/032 382/131 |
| 2007/0076842 A1 * | 4/2007 | Tkaczyk | ................ | A61B 6/032 378/5 |

(Continued)

FOREIGN PATENT DOCUMENTS

CN 1754508 A 4/2006
CN 101004764 A 7/2007

(Continued)

*Primary Examiner* — Thomas R Artman
(74) *Attorney, Agent, or Firm* — McCoy Russell LLP

(57) ABSTRACT

A method and device for X-ray scanning based on dose, comprising: receiving an X-ray dose for scanning set for a region of a subject to be scanned, selecting a scanning and reconstructing technology combination according to said pre-set X-ray dose for scanning wherein the demanded X-ray dose of the selected scanning and reconstructing technology combination satisfies said pre-set X-ray dose for scanning, and scanning said region and implementing a reconstruction accordingly with the selected scanning and reconstructing technology combination to obtain a resultant scanning image.

12 Claims, 3 Drawing Sheets

(56) References Cited

U.S. PATENT DOCUMENTS

| | | |
|---|---|---|
| 2009/0022268 A1 | 1/2009 | Kudo |
| 2011/0129056 A1 | 6/2011 | Allmendinger et al. |
| 2011/0317806 A1 | 12/2011 | Eusemann et al. |
| 2013/0108130 A1 | 5/2013 | Nukui |
| 2015/0085971 A1* | 3/2015 | Braun .................... A61B 6/032 378/8 |

FOREIGN PATENT DOCUMENTS

| | | |
|---|---|---|
| CN | 102573639 A | 7/2012 |
| CN | 103298408 A | 9/2013 |

\* cited by examiner

DOSE BASED X-RAY SCANNING

CROSS-REFERENCE TO RELATED APPLICATIONS

The present application claims priority to Chinese Patent Application No. 201410446011.2, filed on Sep. 2, 2014, the entire contents of which are hereby incorporated by reference for all purposes.

BACKGROUND AND SUMMARY

At present, people are increasingly concerned about the dose for X-ray scanning with a CT scanner system. That is to say, while X-ray scanning a subject (e.g., a patient) with a CT scanner system, it is preferred that the dose for X-ray scanning (e.g., an amount of radiation emitted by X-ray machinery and/or an amount of radiation dose or effective dose applied to a patient) is lower but enough to guarantee the quality of the scanned image. Accordingly, more and more technologies for reducing the dose for X-ray scanning have been disclosed, such as variable current X-ray scanning, automatic voltage selecting X-ray scanning, dose modulated X-ray scanning, and slice tracking technology in start and end phases of a spiral X-ray scanning.

Different image qualities may be obtained with different technologies or combinations thereof. Therefore, the question as to how to obtain a desired image quality without increasing the dose for X-ray scanning has become more and more important.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, MRI, digital X-ray machine, Ultrasound, PET (Positron Emission Tomography), Linear Accelerator, and Biochemistry Analyser. Currently, NMS' products are exported to over 60 countries and regions around the globe, serving more than 5,000 renowned customers. NMS's latest successful developments, such as 128 Multi-Slice CT Scanner System, Superconducting MRI, Linear Accelerator, and PET products, have led China to become a global high-end medical equipment producer. As an integrated supplier with extensive experiences in large medical equipment, NMS has been committed to the study of avoiding secondary potential harm caused by excessive X-ray irradiation to the subject during the CT scanning process. The present disclosure provides methods and systems for configuring X-ray scanning based on the dose of such X-ray scanning (e.g., to achieve a target dose and/or reduce a dose of radiation from the X-ray scanning).

BRIEF DESCRIPTION OF DRAWINGS

Features of the present disclosure are illustrated by way of example and not limited in the following figure(s), in which like numerals indicate like elements, in which.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Figure 1:
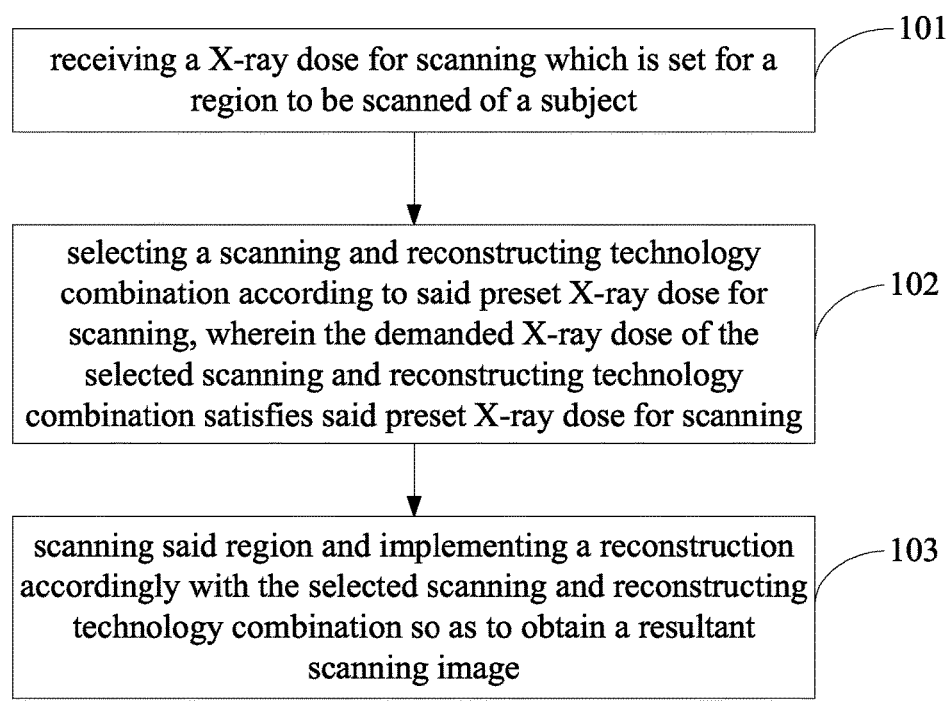
FIG. 1 is a flowchart of a method for X-ray scanning based on dose according to an example of the present disclosure.

Referring to FIG. 1, the present disclosure proposes a method for X-ray scanning based on dose. In block 101, an X-ray dose for scanning, which may be pre-set for a region to be scanned of a subject, is received. In an example, the region of a subject to be scanned, such as the head or neck of the subject, is determined first. Then, for the determined region, the X-ray dose for scanning may be set by an operator according to his or her experience and practical applications scenarios. In other examples, the X-ray dose may be set automatically based on rules, regulations, and/or a database of target X-ray dosages (e.g., organized by body regions, subject demographics/status, purpose of performing the X-ray, etc.). In this way, in the subsequent scanning process, it is possible to drive the whole scanning process with the pre-set X-ray dose for scanning.

In block 102, a scanning and reconstructing technology combination is selected according to said pre-set X-ray dose for scanning (e.g., as set in block 101), wherein the demanded and/or requested X-ray dose of the selected scanning and reconstructing technology combination satisfies said pre-set X-ray dose for scanning.

In an example, the so-called scanning and reconstructing technology combination comprises a scanning technology part and a reconstructing technology part, wherein the scanning technology part may include one or several scanning technologies supported by the CT scanner system, such as automatic voltage selecting scanning, dose modulated scanning technology, etc., and the reconstructing technology part may also include one or several reconstructing technologies supported by the CT scanner system, such as iterative reconstruction, AF (Adaptive Filtering) reconstruction, and image noise reduction algorithm, etc. In other words, after receiving the pre-set X-ray dose for scanning, it is possible to automatically select any combination of scanning technologies and reconstructing technologies supported by the CT scanner system according to said pre-set X-ray dose for scanning.

Furthermore, the expression "satisfy said pre-set X-ray dose for scanning" may refer to taking actions to ensure that said demanded X-ray dose or the X-ray dose consumed by practical scanning is approximately equal to said pre-set X-ray dose for scanning. For example, in view of operating errors, if said demanded X-ray dose is within a range of said pre-set X-ray dose for scanning plus-minus a certain amount, it is possible to consider said demanded X-ray dose satisfies said pre-set X-ray dose for scanning, wherein said certain amount may be arbitrarily set according to practical application scenarios, for example, 5% or even 1% of said pre-set X-ray dose for scanning.

In practical application scenarios, protocol-specified doses for various regions to be scanned, namely, the X-ray doses used for obtaining resultant scanning images for the regions which satisfy diagnostic requirements, may be stored in advance (e.g., in a suitable database, table, or other retrievable data structure). That is, an image obtained by scanning a region according to a scan protocol with the protocol specified dose, and implementing a standard reconstruction may generally satisfy the diagnostic requirements. Before selecting the scanning and reconstructing technology combination, first of all, the pre-stored protocol specified dose for the region to be scanned is acquired. Next, said protocol specified dose is compared with said pre-set X-ray dose for scanning to determine whether said pre-set X-ray dose for scanning is less than said protocol specified dose.

If said pre-set X-ray dose for scanning is not less than the protocol specified dose, it is necessary to evaluate the scanning capability of the CT scanner system and configure system-scanning parameters accordingly. The so-called system scanning capability includes, but is not limited to, bulb tube thermal capacity, bulb tube scanning power, and bulb tube high voltage restrictions, etc. The system scanning capability may be considered while configuring system scanning parameters. For example, the bulb tube power is related to scanning voltage and current. Therefore, while configuring the system scanning parameters, it may be considered that the combination of scanning voltage and current should not exceed the power restriction of bulb tube. Furthermore, a rotational velocity and pitch, etc., might be set based on the above-configured system scanning parameters. In this way, in a case where said pre-set X-ray dose for scanning does not exceed the system scanning capability, it is possible to satisfy said pre-set X-ray dose for scanning by adjusting system scanning parameters such as extending exposure time, and adjusting voltage, current, rotational velocity, and pitch. However, in a case where said X-ray dose for scanning exceeds the system scanning capability, a prompting message may be issued to alert the operator.

On the other hand, if said pre-set X-ray dose for scanning is less than said protocol specified dose, a low dose scanning and reconstructing technology combination supported by the CT scanner system may be selected automatically, wherein said low dose scanning and reconstructing technology combination may include a low dose scanning technology part and/or a low dose reconstructing technology part. The low dose scanning technology part may include one or more low dose scanning technologies supported by the CT scanner system, such as automatic voltage selecting scanning technology, dose modulated scanning technology, organ protection scanning technology, and/or slice tracking technology for start and end phases of spiral scanning. Similarly, the low dose reconstructing technology part may include one or more low dose reconstructing technologies supported by the CT scanner system, such as iterative reconstruction technology, AF reconstruction technology, and image noise reduction algorithm technology, etc.

According to an example of the present disclosure, the process of automatically selecting the low dose scanning and reconstructing technology combination may include one or more of the elements described below. First, if said pre-set X-ray dose for scanning is less than said protocol specified dose, a pre-stored low dose scanning technology such as automatic voltage selecting scanning technology is selected. Then, the X-ray dose to be consumed by using said automatic voltage selecting scanning is determined. That is, the demanded X-ray dose for the selected scanning technology is determined.

Next, it is determined whether the above-mentioned demanded X-ray dose is greater than said pre-set X-ray dose for scanning. If said demanded X-ray dose is greater than said pre-set X-ray dose for scanning on the basis of the selected automatic voltage selecting scanning technology, another low dose scanning technology is further selected, such as dose modulated scanning technology. Then, the X-ray dose to be consumed by utilizing the selected automatic voltage selecting scanning technology simultaneously with dose modulated scanning technology is determined. That is, the demanded X-ray dose for the selected scanning technologies is determined again.

Once more, the above-mentioned demanded X-ray dose is further compared with said pre-set X-ray dose for scanning. If the above-mentioned demanded X-ray dose is still greater than said X-ray dose for scanning, then the method includes continuing to select low dose scanning technologies (e.g., one at a time, repeating one or more of the above-described determinations) until the demanded X-ray dose for the selected low dose scanning technologies satisfies said pre-set X-ray dose for scanning.

Finally, the low dose scanning technology selected as described above is the scanning technology part in the selected scanning and reconstructing technology combination according to said pre-set X-ray dose for scanning in the example.

In this example, after determining the scanning technology part in the scanning and reconstructing technology combination, it is possible to estimate in advance the image noise level of a resultant scanning image obtained by implementing a standard reconstruction based on the combination of the selected scanning technologies, and then determine whether the image noise level is below a pre-stored normal image noise level, wherein said normal image noise level may be an image noise level obtained by applying the protocol specified dose to said region to be scanned. If the pre-estimated image noise level is below said normal image noise level, that is, the quality of the resultant scanning image obtained by a standard reconstruction may satisfy diagnostic requirements, then the standard reconstruction may be selected as the reconstructing technology part in said scanning and reconstructing technology combination. Otherwise, any low dose reconstructing technology is selected as the reconstructing technology part in the scanning and reconstructing technology combination such that the resultant scanning image obtained with the selected scanning and reconstructing technology combination may achieve the normal image noise level.

Although the selection of the scanning and reconstructing technology combination according to said pre-set X-ray dose for scanning is described above with respect to an example in which the scanning technology is selected firstly and the reconstructing technology is selected next, it is understood that the present disclosure is not limited thereto. As long as a combination of a scanning technology part and a reconstructing technology part with a demanded X-ray dose satisfying the pre-set X-ray dose for scanning is selected, the image quality satisfying diagnostic requirements could be selected from all scanning technologies and all reconstructing technologies supported by the CT scanner system, and any way of selection may be applicable to the present disclosure. For example, it is also possible to select any low dose reconstructing technology first, then estimate an allowable reduction degree for dose according to the optimization degree of image noise level by the selected low dose reconstructing technology, and then select one or more low dose scanning technologies according to the estimated allowable dose reduction degree such that the X-ray dose to be consumed by utilizing the selected scanning and reconstructing technology combination can satisfy said pre-set X-ray dose for scanning, and the ultimately obtained resultant scanning images can satisfy the diagnostic requirements.

In addition, in this example, the specific region to be scanned of the subject may be further taken into account while selecting the scanning and reconstructing technology combination. If the regions to be scanned involve eyes, thyroid gland, other sensitive areas, etc., protection for these radiation sensitive organs may be considered when selecting the scanning and reconstructing technology combination. If the subject is a young child, low voltage scanning technologies may be considered. Because the somatotype of the subject would have direct influence on the noise reference for dose modulated scanning technology, which would in turn influence the parameter selection for iterative reconstruction technology, somatotype size of the subject may be considered when a dose modulated scanning technology is selected.

In some examples, it is also possible to consider individual information on the current subject such as age, sex, etc. of the subject while selecting the scanning and reconstructing technology combination. For example, if the subject is a child and the region to be scanned is the belly, the pre-set X-ray dose for scanning may be 0.5 mGy. Since the protocol specified dose for this situation may generally be 2 mGy, selecting one or more low dose scanning technologies to reduce demanded X-ray dose is necessary for accomplishing the X-ray scanning. Specifically, the process of selecting one or more low dose scanning technologies may be as follows:

1. Since the subject is a child, an automatic voltage selecting scanning technology may be considered. For children, a low voltage is generally recommended and it is to be understood that the X-ray dose may be reduced to 1 mGy until now.

2. The spiral scanning is generally selected for belly scanning and the slice slotting tracking technology may be selected. Then, it is to be understood that the X-ray dose may be reduced to 0.8 mGy until now.

3. The dose modulated scanning technology may also be selected to guarantee the consistency of image noise distribution at low X-ray doses for scanning, and the dose may be ultimately reduced to 0.5 mGy to satisfy the requirement of the pre-set X-ray dose for scanning.

In block 103, said region is scanned and a reconstruction is implemented accordingly with the selected scanning and reconstructing technology combination. In addition, when it is impossible (or attempts are unsuccessful) to select a scanning and reconstructing technology combination which could satisfy the pre-set X-ray dose for scanning and the diagnostic requirements from the scanning technologies and reconstructing technologies supported by the CT scanner system, scanning parameters for the system may be adjusted to satisfy said pre-set X-ray dose for scanning. Said system scanning parameters include, but are not limited to, voltage, current, rotational velocity, and pitch, etc. Generally, system restrictions may be taken into account for adjusting system scanning parameters. For example, the bulb tube power is related to scanning voltage and current. Therefore, while configuring the system scanning parameters, it may be considered that the combination of voltage and current may be configured so as to not exceed the power restriction of the bulb tube. Then, a rotational velocity and pitch, etc. might be set based on the above-configured system scanning parameters. If the pre-set X-ray dose for scanning cannot be satisfied yet after adjusting system-scanning parameters, it may indicate that the pre-set X-ray dose for scanning may be too low and could result in a scanning image with an image noise level unable to meet diagnostic requirements. In this case, a prompting message may be issued to alert the operator (e.g., a visual alert presented on a display device, an audio alert presented via a speaker system, etc.).

In this example, the whole scanning process is driven by the pre-set X-ray dose for scanning and a scanning and reconstructing technology combination that can satisfy diagnostic requirements under the pre-set X-ray dose for scanning, which is selected automatically.

Figure 2:
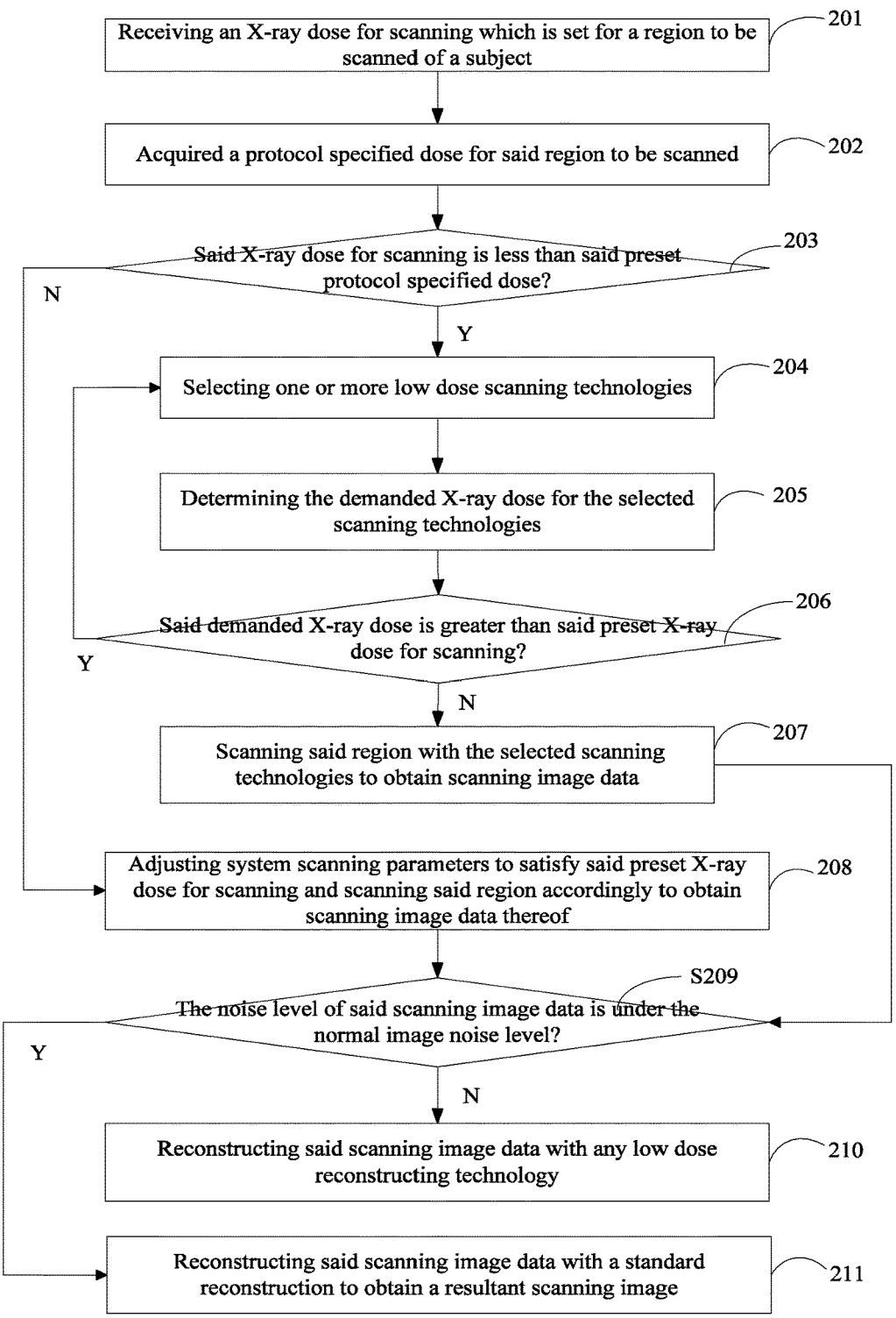
FIG. 2 is a flowchart of a method for X-ray scanning based on dose according to another example of the present disclosure.

Referring to FIG. 2, the present disclosure provides another method for X-ray scanning based on dose. In block 201, an X-ray dose for scanning, which is set based on a region of a subject to be scanned, is received. Specifically, an X-ray dose for scanning may be set for said region to be scanned according to the operator's experience and the practical application scenarios (e.g., manually be the operator and/or automatically by referencing a look-up table, database, and/or other data structure stored in local memory and/or a remote storage device), and then the X-ray dose may be received and used as the driving (e.g., influence) for the whole scanning process (e.g., used to derive other parameters of the scanning process).

In block 202, a protocol-specified dose for said region to be scanned, which is stored in advance, is acquired. In practical application scenarios, protocol-specified doses corresponding to various regions to be scanned, (namely, the X-ray doses required for obtaining resultant scanning images for the regions which satisfy diagnostic requirements), may have been stored in advance in the CT scanner system. That is, an image obtained by scanning a region according to a scan protocol with the protocol-specified dose and implementing a standard reconstruction may generally satisfy the diagnostic requirements.

In block 203, it is determined whether said pre-set X-ray dose for scanning is less than said protocol specified dose. If so, the process proceeds to block 204, and if not, to block 208. In block 204, one or more low dose scanning technologies are selected. In block 205, the X-ray dose to be consumed by utilizing the selected scanning technologies is determined. That is, the demanded X-ray dose for the selected scanning technologies is determined.

In block 206, it is determined whether said demanded X-ray dose is greater than said pre-set X-ray dose for scanning. If so, the process returns to block 204 to select different low dose scanning technologies and determine associated demanded X-ray doses until the demanded X-ray dose is not greater than said pre-set X-ray dose for scanning. Upon determining that the demanded X-ray dose is not greater than said pre-set X-ray dose for scanning, the process proceeds to block 207. In this example, the system automatically selects appropriate scanning technologies according to the pre-set X-ray dose for scanning until the demanded X-ray dose for the selected scanning technologies satisfies said pre-set X-ray dose for scanning. In block 207, said region is scanned with the selected scanning technologies to obtain scanning image data.

In block 208 (performed responsive to determining that the X-ray dose for scanning is not less than the pre-set protocol-specified dose at block 203), system scanning parameters are adjusted to satisfy said pre-set X-ray dose for scanning and said region is scanned accordingly to obtain scanning image data thereof.

When it is determined that said pre-set X-ray dose for scanning is greater than said protocol-specified dose, it is possible to satisfy said pre-set X-ray dose for scanning by adjusting system scanning parameters, such as extending exposure time, and adjusting voltage, current, rotational velocity, and pitch. Of course, as described above, the system's scanning capability should be taken into account while adjusting system scanning parameters, and it should be ensured that said pre-set X-ray dose for scanning does not exceed the system scanning capability. In other words, in case that said pre-set X-ray dose for scanning does not exceed the system scanning capability, it is possible to satisfy said pre-set X-ray dose for scanning by adjusting system scanning parameters. Otherwise, it is recommended to issue a prompting message to alert the operator. In case that said pre-set X-ray dose for scanning is satisfied after adjusting system scanning parameters, said region is scanned to obtain scanning image data thereof.

In block 209, it is determined whether the noise level of said scanning image data is under the normal image noise level corresponding to said protocol specified dose. If so, the process proceeds to block 211 to implement standard reconstruction, otherwise the process proceeds to block 210.

In block 210, said scanning image data is reconstructed with any low dose reconstructing technology.

In block 211, said scanning image data is reconstructed with a standard reconstruction to obtain a resultant scanning image.

In this example, after obtaining scanning image data of said region, it is determined whether the noise level of said scanning image data is below the normal image noise level corresponding to said protocol-specified dose. If the noise level of said scanning image data is below the normal image noise level corresponding to said protocol-specified dose, a standard reconstruction is carried out directly to obtain a resultant scanning image that satisfies diagnostic requirements. If the noise level of said scanning image data is not below the normal image noise level corresponding to said protocol specified dose, said scanning image data is reconstructed with any one low dose reconstructing technology, including but not limited to iterative reconstruction technology, AF reconstruction technology, and image noise reduction algorithm technology.

For example, assuming that the region to be scanned is the lung of an adult, and the noise level of scanning image data is expected to increase by 50% compared to the normal image noise level corresponding to the protocol specified dose by utilizing a low dose scanning technology, then the iterative reconstruction technology should be considered, and appropriate iterative reconstruction parameters should be set to guarantee that the resultant scanning image obtained can satisfy diagnostic requirements. As another example, if the region to be scanned is the lung of an adult, and X-ray scanning is conducted with the protocol specified dose or a higher dose, in view that a strip artefact may be introduced due to noise inconsistency at the site of the lung close to the shoulder, AF reconstruction technology may be utilized to guarantee that the ultimate resultant scanning image can satisfy diagnostic requirements.

In this example, after determining the region to be scanned of the subject, the X-ray dose for scanning is set for said region first, and then the whole scanning process is driven by the pre-set X-ray dose for scanning. That is, a scanning and reconstructing technology combination that can generate a resultant scanning image satisfying diagnostic requirements under the pre-set X-ray dose for scanning is selected automatically.

Figure 3:
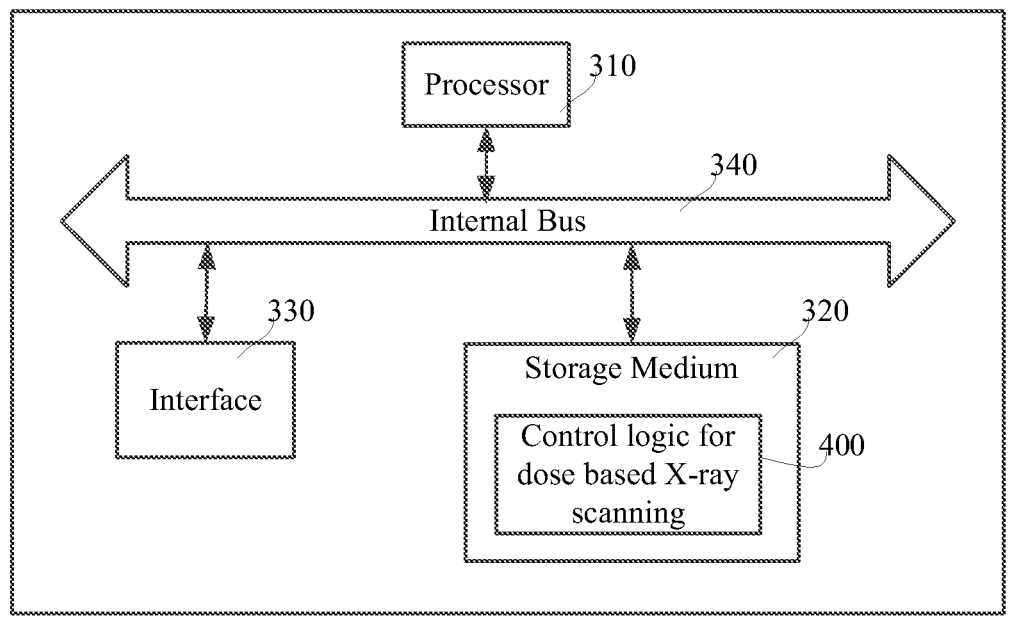
FIG. 3 is a schematic diagram of hardware structure of a device for X-ray scanning based on dose in an example of the present disclosure.

Referring to FIG. 3, which is a schematic diagram of hardware structure of the device for X-ray scanning based on dose in an example of the present disclosure, said device includes a processor 310 such as a CPU and a machine readable storage medium 320, wherein the processor 310 and the machine readable storage medium 320 are typically interconnected via an internal bus 340. In other possible implementations, said device may further include an external interface 330 to be able to communicate with other equipment or components.

In a different example, the machine readable storage medium 320 may be any electronic, magnetic, optical, or other physical storage devices. For example, the machine readable storage medium 320 may be RAM (Radom Access Memory), volatile memory, non-volatile memory, flash memory, memory drive (such as hard disk drive), solid state hard disk, any type of memory disc (such as optical disk, DVD, etc.), or similar storage medium or combination thereof. The machine-readable storage medium 320 may include a non-transitory storage medium that stores instructions executable by the processor 310 to perform one or more of the processes described herein. The processes may be performed by the processor 310 executing the instructions in combination with one or more additional hardware devices, including but not limited to one or more hardware interfaces, actuators, circuits, and/or other elements.

Figure 4:
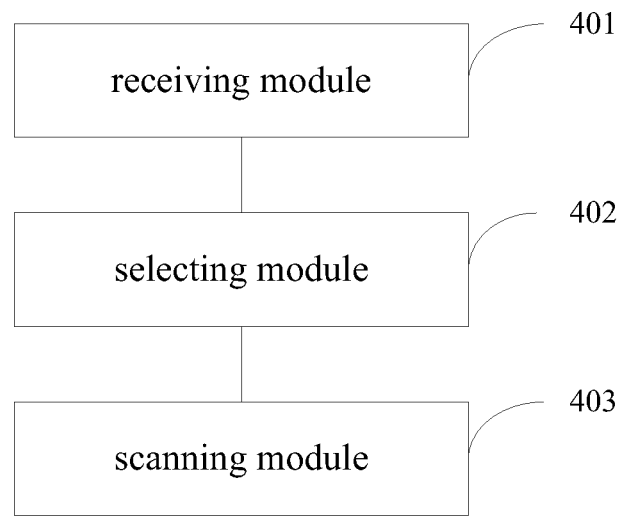
FIG. 4 is a schematic diagram of functional modules of a control logic for X-ray scanning based on dose which corresponds to the example shown in FIG. 1.

Furthermore, the machine-readable storage medium 320 may further store a control logic 400 for X-ray scanning based on dose thereon. As shown in FIG. 4, which is a schematic diagram of functional modules of control logic 400 for X-ray scanning based on dose corresponding to the method shown in FIG. 1, functionally, the control logic 400 for X-ray scanning based on dose may include a receiving module 401 configured to receive an X-ray dose for scanning which is set for a region to be scanned of a subject, a selecting module 402 configured to select a scanning and reconstructing technology combination according to said pre-set X-ray dose for scanning wherein the demanded X-ray dose of the selected scanning and reconstructing technology combination satisfies said pre-set X-ray dose for scanning, and a scanning module 403 configured to scanning said region and implementing an image reconstruction accordingly with the selected scanning and reconstructing technology combination to obtain a resultant scanning image. Said selecting module 402 may include an acquiring submodule configured to acquire a protocol specified dose which is pre-stored for said region to be scanned, a determining submodule configured to determine whether said pre-set X-ray dose for scanning is less than said protocol specified dose, and a selecting submodule configured to determining said scanning and reconstructing technology combination according to the normal image noise level corresponding to said protocol specified dose and said pre-set X-ray dose for scanning, when said pre-set X-ray dose for scanning is less than said protocol specified dose.

In addition, said selecting module may further include an adjusting submodule configured to adjust system scanning parameters to satisfy said pre-set X-ray dose for scanning when said pre-set X-ray dose for scanning is greater than said protocol specified dose and does not exceed the system scanning capability. Said selecting module may further consider information on said subject and/or information on said region to be scanned while selecting the scanning and reconstructing technology combination according to said pre-set X-ray dose for scanning.

In order to satisfy the pre-set X-ray dose for scanning, said control logic 400 may further include a prompting module configured to issue a prompting signal when none of the scanning and reconstructing technology has a demanded X-ray dose satisfying said pre-set X-ray dose for scanning.

In order to further improve image quality of the resultant scanning image, said control logic 400 may further include a determining module configured to determine whether the image noise level of said resultant scanning image is higher than a pre-stored normal image noise level, and a reconstructing module configured to implement a reconstruction on said resultant scanning image with any one low dose reconstructing technology if the image noise level of said resultant scanning image is higher than said normal image noise level.

A process in which the device runs the control logic 400 for X-scanning based on dose will be described further below with respect to software implementation as an example. In this example, the disclosed control logic 400 should be understood as computer executable instructions stored in the machine readable storage medium 320. When the processor 310 on the disclosed device executes the control logic 400, the processor 310 carries out the following operations by invoking instructions of corresponding functional modules of control logic 400 stored on the machine readable storage medium 320: receiving an X-ray dose for scanning which is set for a region to be scanned of a subject, selecting a scanning and reconstructing technology combination according to said pre-set X-ray dose for scanning wherein the demanded X-ray dose of the selected scanning and reconstructing technology combination satisfies said pre-set X-ray dose for scanning, and scanning said region and implementing a reconstruction accordingly with the selected scanning and reconstructing technology combination to obtain a resultant scanning image.

Furthermore, the processor 310 further carries out the following operations by invoking instructions of corresponding functional modules of control logic 400 stored on the machine readable storage medium 320: acquiring a protocol specified dose which is pre-stored for said region to be scanned, determining whether said pre-set X-ray dose for scanning is less than said protocol specified dose, and determining said scanning and reconstructing technology combination according to the normal image noise level corresponding to said protocol specified dose and said pre-set X-ray dose for scanning, when said pre-set X-ray dose for scanning is less than said protocol specified dose.

Furthermore, the processor 310 further carries out the following operations by invoking instructions of corresponding functional modules of control logic 400 stored on the machine readable storage medium 320: determining whether said pres-et X-ray dose for scanning exceeds the system scanning capability when said pre-set X-ray dose for scanning is greater than said protocol specified dose, and adjusting system scanning parameters to satisfy said pre-set X-ray dose for scanning if not.

Furthermore, the processor 310 further carries out the following operations by invoking instructions of corresponding functional modules of control logic 400 stored on the machine readable storage medium 320: selecting a low dose scanning technology in case that the demanded X-ray dose of the selected low dose scanning technology is greater than said pre-set X-ray dose for scanning, going on selecting the next low dose scanning technology until the demanded X-ray dose for the selected low dose scanning technologies satisfies said pre-set X-ray dose for scanning and is assigned as the scanning technology part in said scanning and reconstructing technology combination, and determining whether the noise level obtained by implementing a standard reconstruction based on the data from combination of said selected scanning technologies is below the image noise level corresponding to said protocol specified dose, and if not, selecting a low dose reconstructing technology as the reconstructing technology part in said scanning and reconstructing technology combination.

Furthermore, the processor 310 further carries out the following operations by invoking instructions of corresponding functional modules of control logic 400 stored on the machine readable storage medium 320: further consider information on said subject and/or information on said region to be scanned while selecting the scanning and reconstructing technology combination according to said X-ray dose for scanning, wherein the said information on said subject includes one or more pieces of information of sex, age and somatotype of said subject, and said information on region to be scanned includes whether said region to be scanned is a radiation sensitive organ.

Furthermore, the processor 310 further carries out the following operations by invoking instructions of corresponding functional modules of control logic 400 stored on the machine readable storage medium 320: issuing a prompting signal when none scanning and reconstructing technology has a demanded X-ray dose satisfying said pre-set X-ray dose for scanning.

Furthermore, the processor 310 further carries out the following operations by invoking instructions of corresponding functional modules of control logic 400 stored on the machine readable storage medium 320: determining whether the image noise level of said resultant scanning image is higher than a pre-stored normal image noise level, and implementing a reconstruction on said resultant scanning image with any one low dose reconstructing technology, if the image noise level of said resultant scanning image is higher than said normal image noise level.

The above are only preferred examples of the present disclosure and are not intended to limit the disclosure within the spirit and principles of the present disclosure. Any changes made, equivalent replacements, or improvements in the protection of the present disclosure should be contained within the described range.

The methods, processes, and units described herein may be implemented by hardware (including hardware logic circuitry), software or firmware, or a combination thereof. The term "processor" is to be interpreted broadly to include a processing unit, ASIC, logic unit, or programmable gate array, etc. The processes, methods, and functional units may all be performed by the one or more processors. Reference in this disclosure or the claims to a "processor" should thus be interpreted to mean "one or more processors".

Further, the processes, methods, and functional units described in this disclosure may be implemented in the form of a computer software product. The computer software product is stored in a storage medium and comprises a plurality of instructions for making a processor to implement the methods recited in the examples of the present disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for X-ray scanning based on dose, the method comprising:
   receiving a pre-set X-ray dose for scanning which is set for a region of a subject to be scanned, wherein the pre-set X-ray dose for scanning is set via a manual input;
   acquiring a protocol-specified dose for said region to be scanned, wherein the protocol-specified dose for said region to be scanned is pre-stored in a CT scanner system and a scanning image satisfying diagnostic requirements is to be obtained by scanning said region to be scanned with the protocol-specified dose;
   when said pre-set X-ray dose for scanning is less than said protocol-specified dose, selecting one or more scanning technologies, wherein a demanded X-ray dose of the selected scanning technologies is substantially equal to said pre-set X-ray dose for scanning;
   scanning said region with the selected scanning technologies to obtain scanning image data;
   determining a reconstructing technology according to a noise level of the scanning image data and a normal image noise level, wherein the normal image noise level indicates an image noise level obtained by scanning said region with the protocol-specified dose; and
   performing the reconstructing technology on the scanning image data so as to obtain a resultant scanning image with a noise level of the resultant scanning image equal to or below the normal image noise level.

2. The method according to claim 1, further comprising:
   when said pre-set X-ray dose for scanning is greater than said protocol-specified dose and less than a system scanning capability,
      adjusting system scanning parameters such that the system scanning capability for the adjusted system scanning parameters is substantially equal to said pre-set X-ray dose for scanning, wherein the system scanning capability is determined by the system scanning parameters.

3. The method according to claim 1, wherein selecting the one or more scanning technologies comprises:
   selecting a scanning technology;
   in a case where the demanded X-ray dose of the selected scanning technology is greater than said pre-set X-ray dose for scanning, continuing to select a next scanning technology until the demanded X-ray dose for the selected scanning technology is substantially equal to said pre-set X-ray dose for scanning.

4. The method according to claim 3, wherein the one or more scanning technologies are selected based on information on one or more of said subject and said region to be scanned.

5. The method according to claim 4, wherein
   said information on said subject includes one or more pieces of information of sex, age, and somatotype of said subject, and
   said information on said region to be scanned includes whether said region to be scanned is a radiation sensitive organ.

6. The method according to claim 1, further comprising:
   issuing a prompting signal when no scanning and reconstructing technology has the demanded X-ray dose satisfying said pre-set X-ray dose for scanning.

7. A device for X-ray scanning based on dose, the device comprising:
   a processor which invokes machine readable instructions corresponding to a control logic for X-ray scanning based on dose stored on a storage medium and executes the instructions to:
      receive a pre-set X-ray dose for scanning which is set for a region of a subject to be scanned, wherein the pre-set X-ray dose for scanning is set via a manual input;
      acquire a protocol-specified dose for said region to be scanned, wherein the protocol-specified dose for said region to be scanned is pre-stored in a CT scanner system and a scanning image satisfying diagnostic requirements is to be obtained by scanning said region to be scanned with the protocol-specified dose;
      when said pre-set X-ray dose for scanning is less than said protocol-specified dose, select one or more scanning technologies, wherein a demanded X-ray dose of the selected scanning technologies is substantially equal to said pre-set X-ray dose for scanning;
      scan said region with the selected scanning technologies to obtain scanning image data;
      determine a reconstructing technology according to a noise level of the scanning image data and a normal image noise level, wherein the normal image noise level indicates an image noise level obtained by scanning said region with the protocol-specified dose; and
      perform the reconstructing technology on the scanning image data so as to obtain a resultant scanning image with a noise level of the resultant scanning image equal to or below the normal image noise level.

8. The device according to claim 7, wherein said instructions further cause the processor to:
   when said pre-set X-ray dose for scanning is greater than said protocol-specified dose and less than a system scanning capability,
      adjust system scanning parameters such that the system scanning capability for the adjusted system scanning parameters is substantially equal to said pre-set X-ray dose for scanning, wherein the system scanning capability is determined by the system scanning parameters.

9. The device according to claim 7, wherein said instructions further cause the processor to:

select a scanning technology;

in a case where the demanded X-ray dose of the selected scanning technology is greater than said pre-set X-ray dose for scanning, continuing to select a next scanning technology until the demanded X-ray dose for the selected scanning technology is substantially equal to said pre-set X-ray dose for scanning.

10. The device according to claim 9, wherein said instructions further cause the processor to:

select the one or more scanning technologies based on information on one or more of said subject and said region to be scanned.

11. The device according to claim 10, wherein said information on said subject includes one or more pieces of information of sex, age, and somatotype of said subject, and said information on said region to be scanned includes whether said region to be scanned is a radiation sensitive organ.

12. The device according to claim 7, wherein said instructions further cause the processor to:

issue a prompting signal when no scanning and reconstructing technology has the demanded X-ray dose satisfying said pre-set X-ray dose for scanning.

* * * * *